(12) United States Patent
Briman

(10) Patent No.: US 9,000,769 B2
(45) Date of Patent: Apr. 7, 2015

(54) CONTROLLED ELECTROCHEMICAL ACTIVATION OF CARBON-BASED ELECTRODES

(75) Inventor: Mikhail Briman, Sunnyvale, CA (US)

(73) Assignee: Proxim Diagnostics, Sunnyvale, CA (US)

(*) Notice: Subject to any disclaimer, the term of this patent is extended or adjusted under 35 U.S.C. 154(b) by 534 days.

(21) Appl. No.: 13/511,143

(22) PCT Filed: Oct. 29, 2010

(86) PCT No.: PCT/US2010/054591
§ 371 (c)(1),
(2), (4) Date: May 22, 2012

(87) PCT Pub. No.: WO2011/062738
PCT Pub. Date: May 26, 2011

(65) Prior Publication Data
US 2012/0242345 A1    Sep. 27, 2012

Related U.S. Application Data

(60) Provisional application No. 61/263,774, filed on Nov. 23, 2009.

(51) Int. Cl.
*G01N 27/02*     (2006.01)
*G01N 27/327*    (2006.01)

(52) U.S. Cl.
CPC .................................. *G01N 27/3276* (2013.01)

(58) Field of Classification Search
None
See application file for complete search history.

(56) References Cited

U.S. PATENT DOCUMENTS

| | | | |
|---|---|---|---|
| 5,324,400 A * | 6/1994 | Eliash et al. ................... | 205/794 |
| 2005/0130296 A1 | 6/2005 | Pisharody et al. | |
| 2006/0166090 A1 | 7/2006 | Grigorian et al. | |
| 2006/0205061 A1 | 9/2006 | Roukes | |
| 2009/0030293 A1 | 1/2009 | Cooper et al. | |
| 2009/0159464 A1* | 6/2009 | Hyland et al. ................ | 205/790 |
| 2009/0240166 A1 | 9/2009 | Wang et al. | |
| 2009/0253149 A1 | 10/2009 | Ahrens et al. | |

OTHER PUBLICATIONS

Bleda-Martínez, et al., Electrochemical Methods to Enhance the Capacitance in Activated Carbon/Polyaniline Composites, Journal of The Electrochemical Society, 155 (10) 1-XXXX (2008).*

(Continued)

*Primary Examiner* — Melissa Koval
*Assistant Examiner* — Daniel Miller
(74) *Attorney, Agent, or Firm* — Jeffrey Jue; Catalyst IP Group

(57) ABSTRACT

Certain embodiments of the present application describe a process to perform activation of carbon based electrodes in a controlled manner, where the degree of activation is monitored and calculated simultaneously with the ongoing activation process. Such an approach is intended to improve the reproducibility of electrodes that may include, but are not limited to, the following parameters: electrochemical capacitance, electrochemical transfer coefficient, amperometric response to enzymatic reactions.

8 Claims, 10 Drawing Sheets

110

(56) References Cited

OTHER PUBLICATIONS

Nian, et al., Nitric Acid Modification of Activated Carbon Electrodes for Improvement of Electrochemical Capacitance, Journal of The Electrochemical Society, 149 (8) A1008-A1014 (2002).*

Ranganathan, et al., Facile Preparation of Active Glassy Carbon Electrodes with Activated Carbon and Organic Solvents, Anal. Chem., 71, 3574-3580 (1999).*

Wang, J., et al., Electrochemical activation of screen-printed carbon strips. Analyst, 1996. 121(3): p. 345-350.

Anjo, D., et al., Electrochemical activation of carbon electrodes in base: Minimization of dopamine adsorption and electrode capacitance. Anal. Chem., 1989. 61: p. 2603-2608.

Beilby, A.L., W. Brooks, and G.L. Lawrence, Comparison of the Pyrolytic Carbon Film Electrode with the Wax-Impregnated Graphite Electrode. Analytical Chemistry, 1964. 36(1): p. 22-26.

* cited by examiner

150

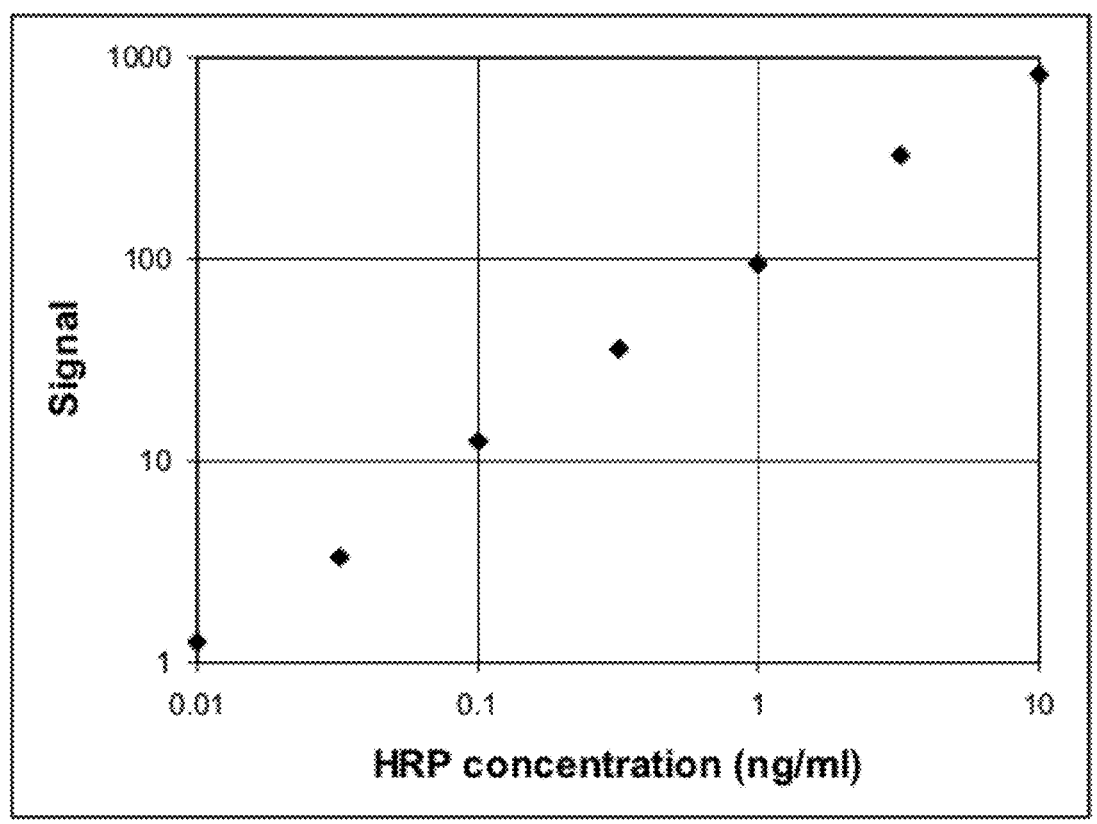

FIG. 8

| Measurement | Controlled activation | | | Fixed number of cycles | | |
|---|---|---|---|---|---|---|
| | Device | Pad | I (nA) | Device | Pad | I (nA) |
| 1 | 1 | 1 | 107.374 | 1 | 1 | 120.362 |
| 2 | 2 | 1 | 105.4415 | 1 | 2 | 111.779 |
| 3 | 1 | 2 | 102.1585 | 2 | 2 | 109.105 |
| 4 | 2 | 2 | 101.571 | 2 | 1 | 106.216 |
| 5 | 1 | 3 | 98.7965 | 2 | 3 | 105.564 |
| 6 | 2 | 3 | 97.9965 | 1 | 3 | 105.173 |
| 7 | 2 | 4 | 96.9615 | 1 | 4 | 103.918 |
| 8 | 3 | 1 | 96.728 | 2 | 4 | 101.806 |
| 9 | 1 | 4 | 96.1485 | 1 | 5 | 98.205 |
| 10 | 2 | 5 | 94.1695 | 1 | 7 | 93.541 |
| 11 | 1 | 5 | 93.918 | 1 | 6 | 92.789 |
| 12 | 3 | 3 | 93.821 | 1 | 8 | 92.652 |
| 13 | 1 | 7 | 93.325 | 3 | 3 | 91.772 |
| 14 | 1 | 6 | 93.084 | 3 | 2 | 89.611 |
| 15 | 1 | 8 | 92.7605 | 2 | 5 | 89.027 |
| 16 | 2 | 6 | 92.427 | 3 | 1 | 88.564 |
| 17 | 3 | 2 | 91.344 | 2 | 6 | 88.419 |
| 18 | 2 | 7 | 90.0865 | 2 | 7 | 85.48 |
| 19 | 2 | 8 | 88.158 | 3 | 4 | 84.391 |
| 20 | 3 | 6 | 85.034 | 2 | 8 | 82.709 |
| 21 | 3 | 5 | 84.9905 | 3 | 5 | 74.186 |
| 22 | 3 | 4 | 84.877 | 3 | 6 | 72.222 |
| 23 | 3 | 7 | 82.097 | 3 | 7 | 66.158 |
| 24 | 3 | 8 | 80.972 | 3 | 8 | 63.598 |
| | | Median | 93.573 | | Median | 92.212 |
| | | SD | 6.933751 | | SD | 14.34558 |
| | | CV% | 7.41% | | CV% | 15.56% |

CONTROLLED ELECTROCHEMICAL ACTIVATION OF CARBON-BASED ELECTRODES

FIELD OF THE INVENTION

This application claims priority to U.S. Provisional Application No. 61/263,774, filed Nov. 23, 2009 and entitled "CONTROLLED ELECTROCHEMICAL ACTIVATION OF CARBON-BASED ELECTRODES," which is hereby incorporated herein by reference.

FIELD OF THE INVENTION

The present invention relates generally to an apparatus and process to perform activation of electrodes in a controlled manner.

BACKGROUND OF THE INVENTION

In electrochemistry, activation of an electrode refers to a process that improves the electrochemical properties of a given electrode. For example, activation could affect the rate of electrochemical reaction. A possible method for such activation on carbon-based electrodes is an electrochemical one, where the process involves placing an electrode in a liquid medium at a selected potential as compared to the reference electrode. It has been reported that such a procedure both cleans the electrode surface and for various carbon-based materials introduces functional groups that may include carboxyl or quinone through faradic type reaction; those reactions that involve electron transfer from electrolyte to electrode.

Reported electrochemical activation procedures involve glassy carbon electrodes, pyrolytic carbon films, and screen-printed electrodes. The prior art describes the electrochemical activation (hereafter "activation") process as applying a certain fixed potential to the working electrode for a fixed amount of time.

SUMMARY OF THE INVENTION

The present invention describes a process and apparatus by which electrochemical activation is combined with some other measurement technique that can assess the degree of activation.

In certain embodiments of the present invention, a process may employ measurement of electrochemical capacitance, because this value may increase as more electrochemically active surface groups are introduced during a given activation process. The activation process may be allowed to continue until a target degree of activation is met, which may be some predefined electrode capacitance value.

In certain embodiments of the present invention, novel electrode apparatuses may be employed to perform the aforementioned processes.

Certain embodiments of the present invention may provide an advantage over alternate methods with respect to improved reproducibility of electrodes. For example, where the capacitance of an electrode depends both on electrochemically available area of an electrode and the number of surface functional groups, electrodes with narrower distribution of their given capacitances may translate to better reproducibility for other electrochemical reactions, compared with another group of electrodes where their capacitance values form a much broader distribution.

In certain embodiments of the present invention an electrode may be a carbon-based electrode, while in other embodiments of the present invention an electrode may comprising a different conductive materials (e.g., gold, platinum, palladium, etc.).

Other features and advantages of the invention will be apparent from the accompanying drawings and from the detailed description. One or more of the above-disclosed embodiments, in addition to certain alternatives, are provided in further detail below with reference to the attached figures. The invention is not limited to any particular embodiment disclosed; the present invention may be employed in not only sensor applications, but in other applications as well. As used herein, "substantially" shall mean that at least 40% of components are of a given type.

BRIEF DESCRIPTION OF THE DRAWINGS

The invention is better understood from reading the following detailed description of the preferred embodiments, with reference to the accompanying figures in which:

FIG. 7 is a graph showing the response of 8-plex device to different concentrations of HRP (log-log scale) according to certain embodiments of the present invention (note: the ratio of the response to 0.01 ng/ml to 0 ng/ml is approximately ten); and FIG. 8 is a table showing a performance comparison between controlled and fixed number of cycles activation protocols.

Features, elements, and aspects of the invention that are referenced by the same numerals in different figures represent the same, equivalent, or similar features, elements, or aspects in accordance with one or more embodiments of the system. Those of ordinary skill in the art will appreciate that features, elements and aspects of the invention depicted in the figures in a similar or identical manner may be similar or identical, even if, for example, a plurality of such features, elements and aspects are not individually labeled.

DETAILED DESCRIPTION OF THE EMBODIMENTS

An electrode apparatus according to certain embodiments of the present invention comprised an 8 pad electrode screen-printed sensor ("8-plex device"). This device was employed to demonstrate activation processes according to certain embodiments of the present invention.

Figure 1A:
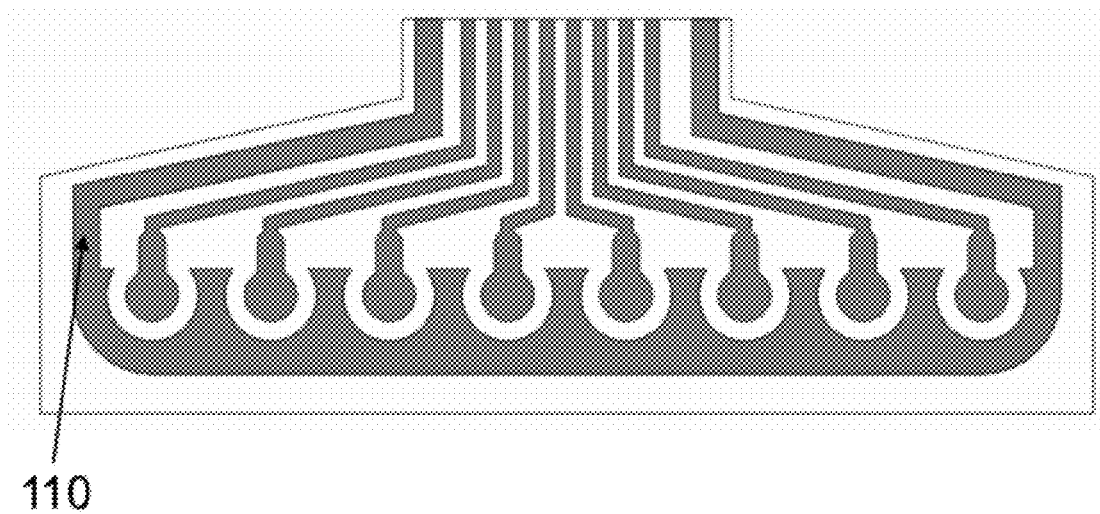
FIGS. 1A-1E are schematic representations of an electrode apparatus and device fabrication process according to certain embodiments of the present invention.

Referring to FIG. 1A, the 8-plex device may be fabricated by first screen-printing silver ink contact traces 110 on a plastic flexible substrate.

Figure 1B:
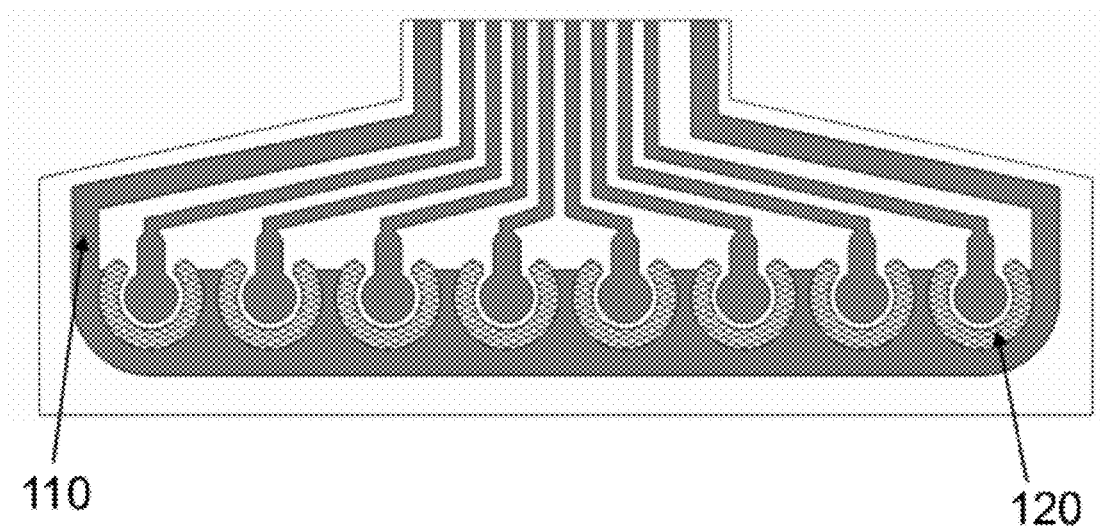

Referring to FIG. 1B, silver/silver chloride (Ag/AgCl) inks may then be screen-printed to form a reference electrode 120.

Figure 1C:
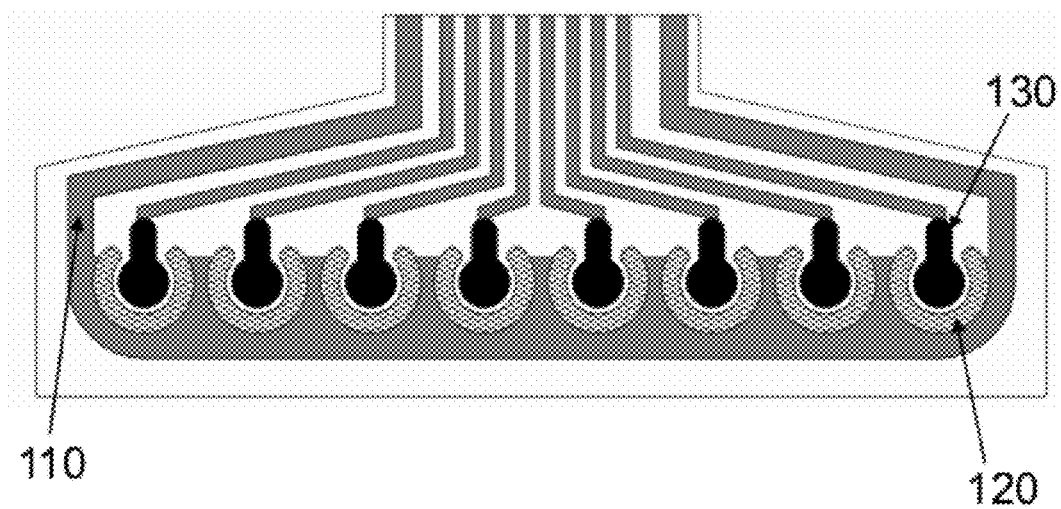

Referring to FIG. 1C, carbon inks (e.g., proprietary inks) may then be screen-printed to form 8 sensor pads (working electrodes, sensor electrodes) 130.

Figure 1D:
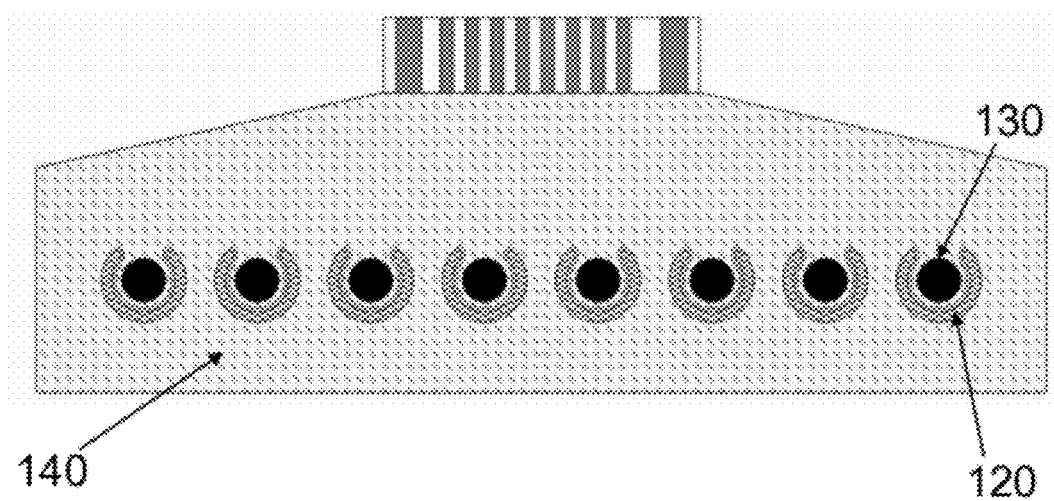

Referring to FIG. 1D, an insulation layer 140 may then be screen-printed, for example, to have only sensing pads and reference electrodes be exposed to liquid.

Figure 1E:
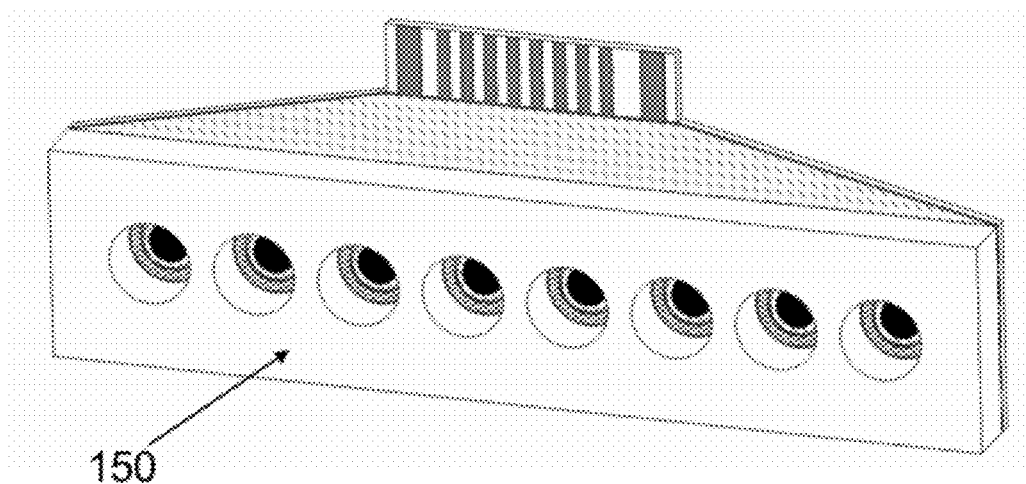

Referring to FIG. 1E, a plastic top part 150 with 8 openings may then be glued on top of the plastic to form 8 isolated wells for liquid application.

Electrode apparatuses, e.g., 8-plex devices as described above, according to certain embodiments of the present invention may be connected to an electronic measuring setup that allows setting the user-defined voltage V (V) on the reference electrode and measuring individual pad currents I (A).

Figure 2:
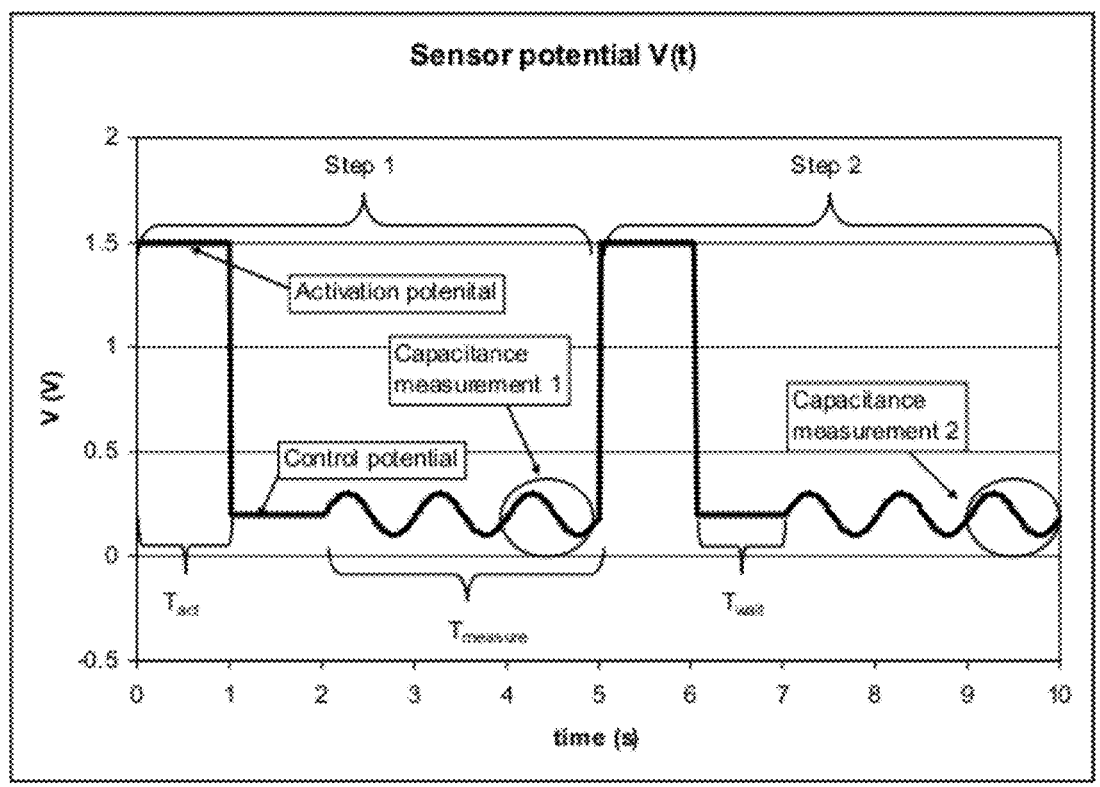
FIG. 2 is a graph of sensor potential as a function of time during activation process according to certain embodiments of the present invention.

Referring to FIG. 2, in certain embodiments of the present invention controlled activation may be represented by the following procedure. First, a sensor may be exposed to an aqueous solution. Any number of aqueous solutions may be used, including but not limited to phosphate buffered saline (PBS) pH 7.2 and phosphate-citrate buffer pH 5.0, without departing from the scope of the present invention. Next, the potential on the sensor may be applied in the cyclic manner as shown in FIG. 2.

After application of activation potential ($V_{act}$) versus the potential of the reference electrode for a certain period ($T_{act}$), the potential may be brought back down to the value ($V_{control}$) where the sensor does not normally participate in faradic reactions with electrolyte, and the controlling capacitance measurement is performed. Finally, after staying there for a predefined amount of time ($T_{wait}$) at the controlled potential, a small sine wave may be superimposed around $V_{control}$ for a time that would be necessary enough to measure the capacitance ($T_{measure}$). For a given measurement, both sensor potential V(t) and current I(t) may be recorded, and at the end of each cycle the last sine wave may be analyzed and its amplitude $I_{ampl}$, offset $I_{ofst}$, and phase shift ($\phi$) between voltage and current may be calculated. The capacitance may then be estimated by the following equation:

$$C = \frac{I_{ampl}}{V_{ampl} \cdot 2 \cdot \pi \cdot f \cdot \sin(\varphi)} \quad \text{EQ. 1}$$

where $V_{ampl}$ is the amplitude of the applied potential wave, and f is the frequency.

The activation cycle may be ended when the capacitance becomes greater or equal to some predefined target value $C_{final}$.

In certain sample embodiments of the present invention, preferred values of the parameters mentioned above may be set but not limited to $V_{act}$=1.5 V, $T_{act}$=1 sec, $V_{control}$=0.2 V, $T_{wait}$=2 sec, $T_{measure}$=2 sec, f=10 Hz, $V_{ampl}$=0.015 V.

Figure 3:
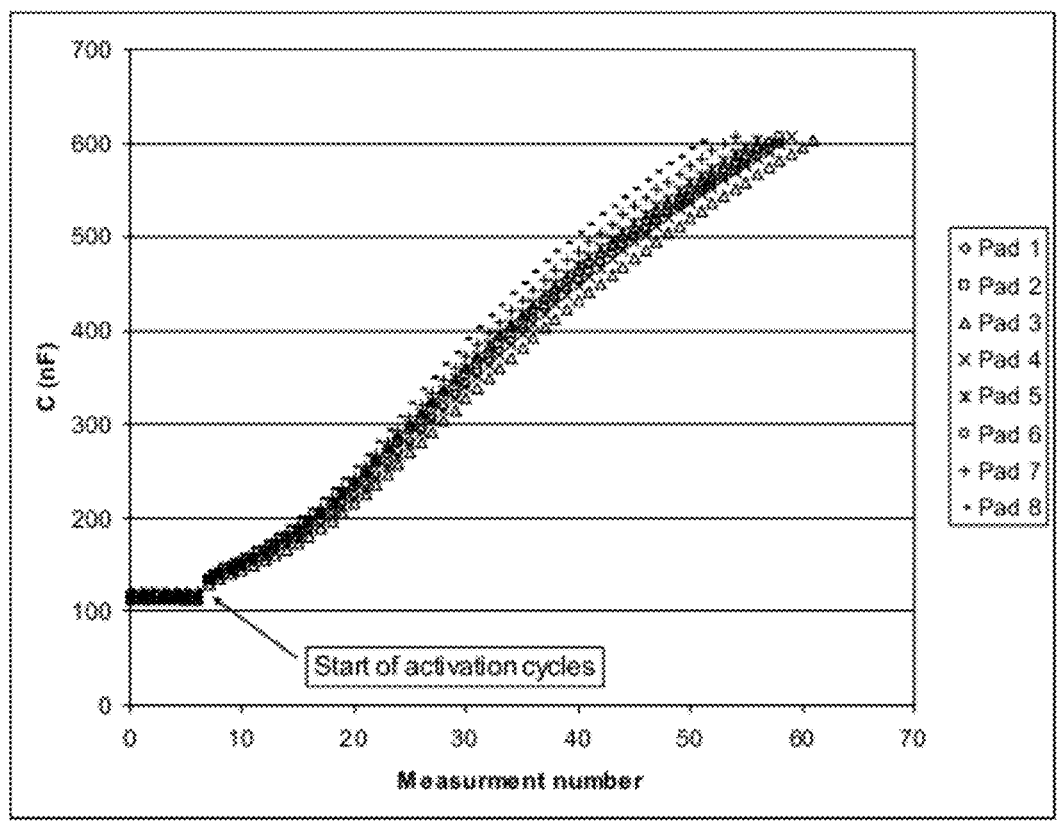
FIG. 3 is a graph of capacitance of all 8 pads of an experimental embodiment as a function of activation cycle according to certain embodiments of the present invention (note: the activation process started on the 7th measurement)

Referring to FIG. 3, real-time controlled activation data with $C_{final}$ set to 600 nF (e.g., pads would target this value as their final capacitance) demonstrates functional aspects of certain embodiments of the present invention. Specifically, a key merit of such embodiments is that the pads do not reach the target capacitance value at the same time, emphasizing the possible importance of activation process control for each individual pad.

Figure 4A:
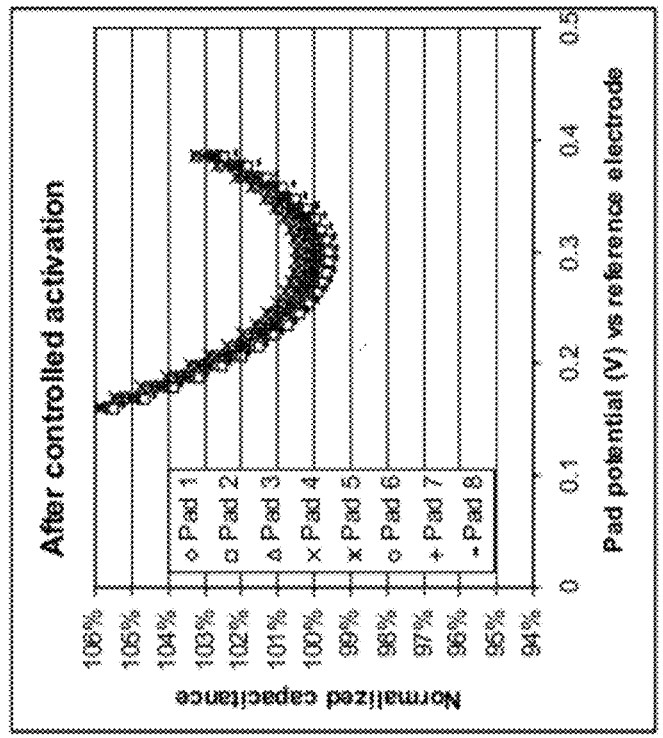
FIGS. 4A and 4B are graphs showing the normalized capacitance for pads before and after activation according to certain embodiments of the present invention.
Figure 4B:
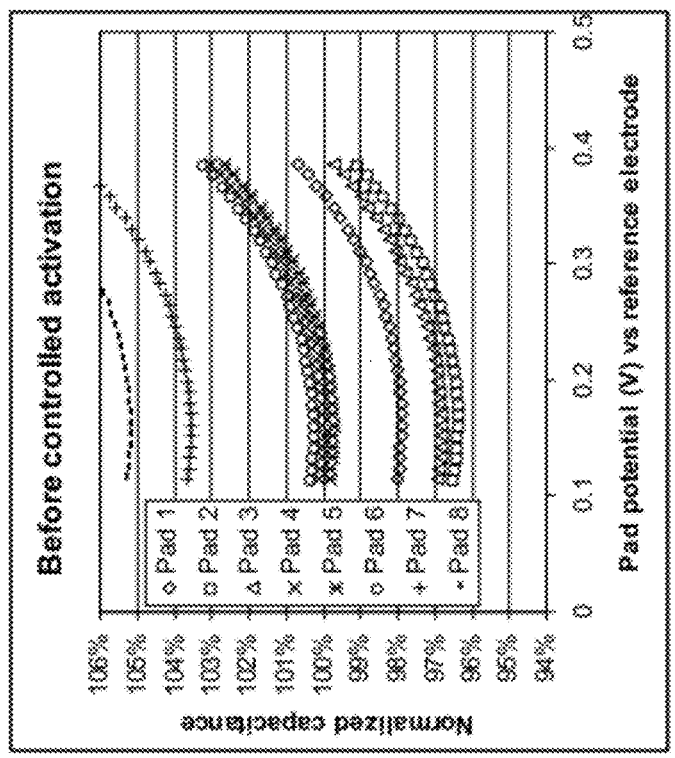

Referring to FIG. 4, in addition to the real-time data, the capacitance of 8-plex device was measured at different voltages before and after activation process for certain embodiments of the present invention. The data was then normalized to the average capacitance of all 8 pads.

Analysis of the experiment, corresponding to certain embodiments of the present invention, indicates that the data set of the minimal capacitances of 8 pads before activation process had coefficient of variation (CV %) approximately 3.1%. After controlled activation procedure, CV % has been reduced to 0.4% or roughly 8-fold improvement in the variability of their capacitance values. Further improvements in the algorithm of the controlled activation process described above may lead to even greater reductions of capacitance variability amongst, for example, large numbers of electrodes.

A controlled activation procedure according to certain embodiments of the present invention, e.g., as described above, may be employed to improve the precision of a given immunological electrochemical biosensor that has carbon-based electrodes. The sample embodiment below describes a HRP (horseradish peroxidase) enzyme sensor that served as a model system.

Construction of the Immunological Sensor

Immunological sensors according to certain further embodiments of the present invention were constructed by first exposing each pad of an 8-plex device to 100 µL of PBS buffer containing anti-HRP antibodies. Next, some devices were controlled activated to 1000 nF per pad, others to 400 nF per pad, while the rest were not activated (the "as is" capacitance was approximately 115 nF per pad). The activation to higher than 1000 nF capacitance values appeared to be unreasonable since it could lead to pad degradation and undesirable higher response to zero control. After that, all devices were left at room temperature for 2 hours to allow antibody adsorption to the pad surface. Finally, all devices were washed and blocked for 1 hour at room temperature with a protein-based blocking buffer to prevent non-specific background.

To demonstrate the functionality of the aforementioned 8-plex device as an immunological sensor subsequent to activation, 8 pads of the 8-plex device were exposed to 10, 3.2, 1, 0.32, 0.1, 0.032, 0.010, 0 ng/mL HRP, such that the 8th pad served as a negative (zero) control. After 40 minute incubation with target (HRP) at room temperature, the 8-plex devices were washed and the fluid wells were filled with tetramethylbenzidine (TMB) based substrate that generates electrochemically active product in the presence of HRP.

Figure 5:
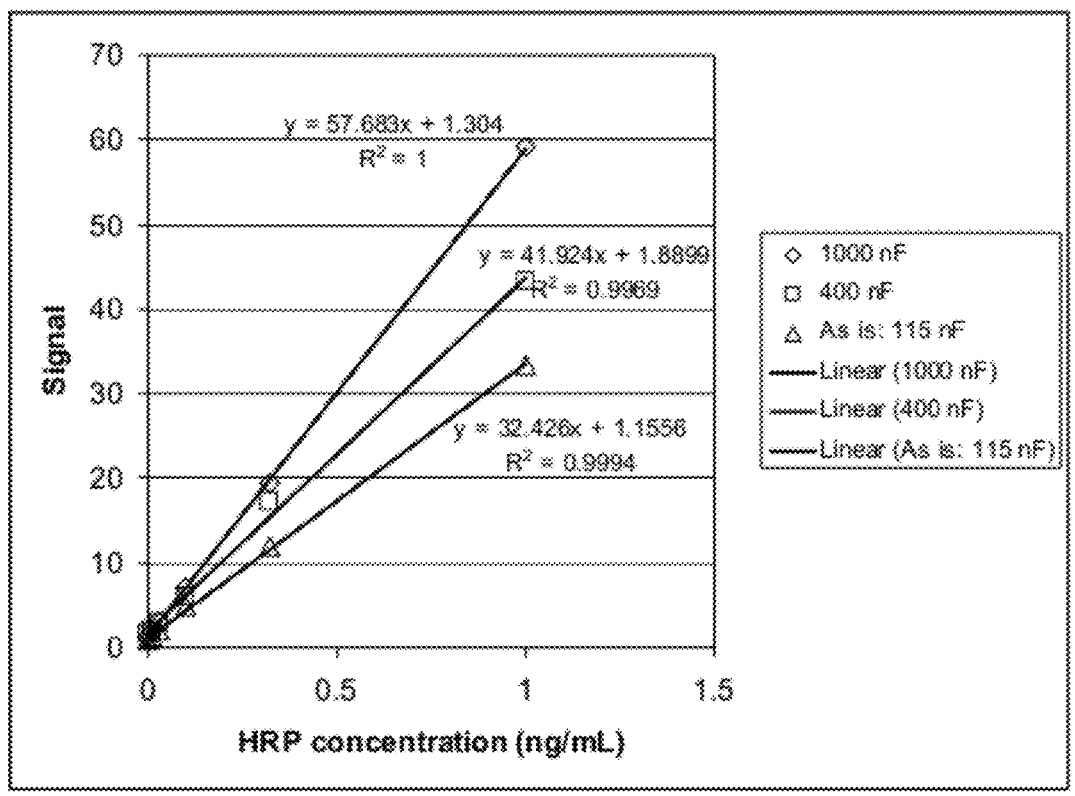
FIG. 5 is a graph showing the response of the differently activated 8-plex devices to HRP according to certain embodiments of the present invention.

Referring to FIG. 5, device responses indicate that in certain embodiments of the present invention, controlled activation to 1000 nF may provide the best sensitivity (higher slope) while keeping background signal almost as low as in the case of non-activated device. Based on this information, for the experiments described below, $C_{final}$ was set to 1000 nF.

Figure 6A:
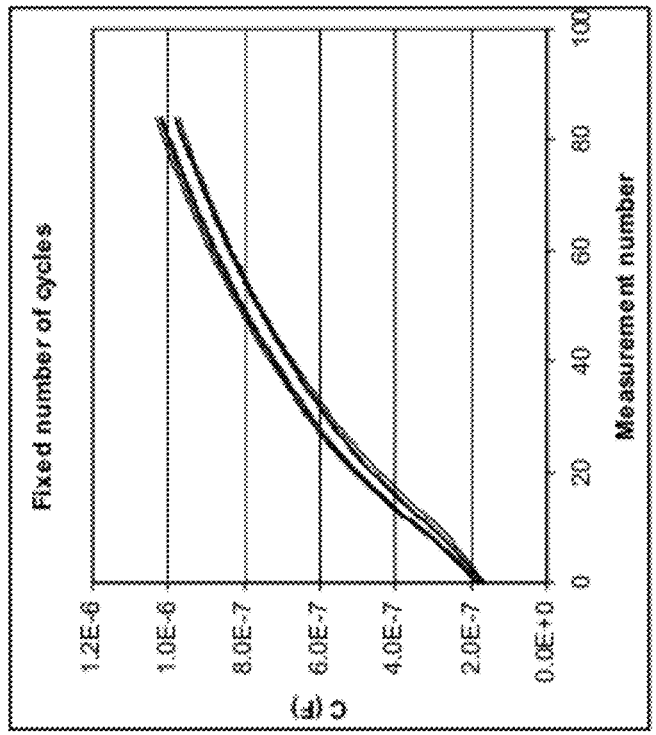
FIGS. 6A and 6B are graphs showing sample real-time activation data (Controlled activation (FIG. 6A) versus Fixed number of cycles (FIG. 6B)) according to certain embodiments of the present invention.
Figure 6B:
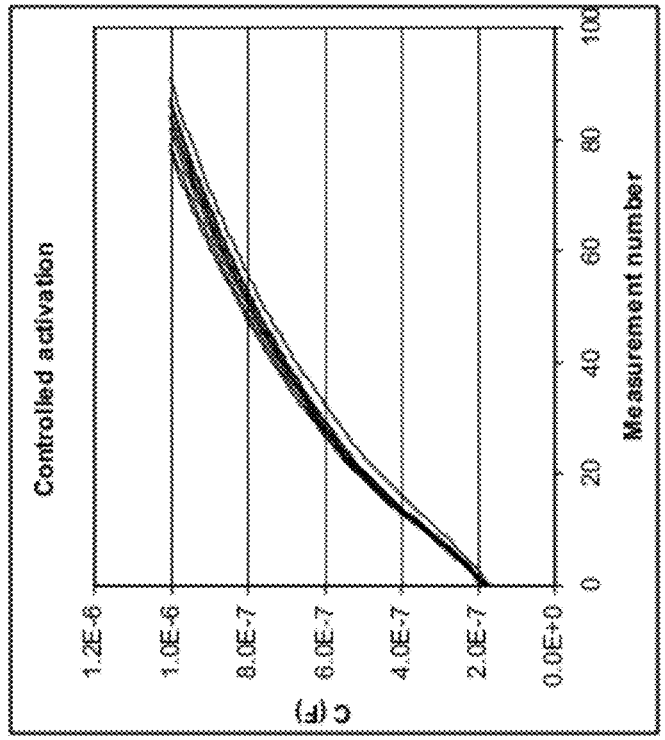

Referring to FIGS. 6A and 6B, to demonstrate precision improvement according to certain embodiments of the present invention, immunological sensors were constructed by first exposing each pad of 8-plex device to 100 µL of PBS buffer containing anti-HRP antibodies and then some of 8-plex devices went through a controlled activation procedure for each pad with Cfinal set to 1000 nF. Other 8-plex devices were activated for the fixed number of cycles without individual pad control to reach average 8-plex pad capacitance 1000 nF. Devices were left at room temperature for 2 hours to allow antibody adsorption to the pad surface. After that, devices were washed and blocked for 1 hour at room temperature with a protein-based blocking buffer to prevent non-specific background. In both controlled and fixed number of cycles activation protocols, a dose response after incubation with HRP for 60 minutes were very similar with a typical data shown in FIG. 8.

Referring to FIG. 7, response data of an 8-plex device according to certain sample embodiments of the present invention to different concentrations of HRP (log-log scale) indicated that a ratio of the response to 0.01 ng/ml to 0 ng/ml is approximately ten.

In order to evaluate the precision improvement, the group of six 8-plex devices was exposed to 1 ng/ml HRP. Out of six sample devices, three went through controlled activation procedure, while the other three were activated for the fixed number of cycles. Results are summarized in FIG. 8, and indicate a coefficient of variation (CV %) for all pads for the group that went through controlled activation protocol was approximately two fold lower, 7.41% as compared to 15.56%, or rather the precision was twice as tight compared with the uncontrolled group. Those of ordinary skill in the art will appreciate that with additional modification to the controlled activation method it may be possible to further improve the precision of the immunological sensor.

Larger scale embodiments of the controlled activation process described above are within the scope of the present invention. For example, embodiments of the present invention for electrochemical sensors with carbon-based electrodes may include, but are not limited to, the following routine. A set of screen-printed carbon-based electrodes is placed in the controlled environment chamber (for example 37 C, 50% relative humidity) with each sensor connected to an electronic setup capable of performing controlled activation procedure described above. Next, a solution containing the bio-functionalization reagents (for example antibodies in PBS buffer) is introduced on top of the sensors and controlled activation procedure is carried out for each sensor. The quality control (QC) is performed at the same time: If a sensor fails to reach predefined Cfinal value within certain range of activation cycles, then this sensor is considered as failed and will not be used for the next steps. The sensors that pass the QC step will go through the next manufacturing steps that can include but not limited to non-specific binding blocking, placing of dried reporter antibodies next to sensor area, integration of the electrodes with plastic sample delivery cartridges, and packaging integrated cartridges for the long-term storage.

The present invention has been described above with reference to preferred features and embodiments. Those skilled in the art will recognize, however, that changes and modifications may be made in these preferred embodiments without departing from the scope of the present invention. For example, those skilled in the art will recognize that although exemplary embodiments have been described above with respect to carbon-based electrodes, the present invention is also applicable to electrodes comprising other conductive materials (e.g., gold, platinum, palladium, etc.).

What is claimed is:

1. A process for producing an electrochemical sensor, comprising:
   exposing a carbon-based sensor electrode and a reference electrode to an aqueous solution;
   cyclically applying an electric potential to the sensor electrode versus the reference electrode, wherein cyclically applying the electric potential comprises:
      during a first time period, setting the electric potential to a first potential level at which the carbon-based sensor electrode substantially participates in faradic reactions with electrolytes in the aqueous solution; and
      during a second time period after the first time period, setting the electric potential to a second potential level at which the carbon-based sensor electrode does not substantially participate in faradic reactions with electrolytes in the aqueous solution;
   measuring an electrochemical capacitance between the carbon-based sensor electrode and the reference electrode during the second time period; and
   stopping the cyclical application of the electric potential when the measured electrochemical capacitance reaches a predefined electrochemical capacitance value.

2. The process of claim 1, further comprising introducing functional groups to a surface of the carbon-based sensor electrode through faradic type reactions.

3. The process of claim 2, wherein the process increases electrochemical property reproducibility of the surface of the sensor electrode compared to a process in which the electric potential is applied for a fixed number of cycles.

4. The process of claim 1, wherein the process increases electrochemical property reproducibility of a surface of the sensor electrode compared to a process in which the electric potential is applied for a fixed number of cycles without regard to electrochemical capacitance.

5. An electrochemical sensor produced by the process of claim 1.

6. The electrochemical sensor of claim 5, wherein functional groups are attached to a surface of the carbon-based sensor electrode.

7. The sensor of claim 6, wherein the functional groups comprise at least one of carboxyl and quinone.

8. The electrochemical sensor of claim 7, wherein the electrochemical sensor is an immunological electrochemical biosensor.

* * * * *